United States Patent [19]

Rembaum

[11] 4,014,798

[45] Mar. 29, 1977

[54] INSOLUBLE POLYELECTROLYTE AND ION-EXCHANGE HOLLOW FIBER IMPREGNATED THEREWITH

[75] Inventor: Alan Rembaum, Altadena, Calif.

[73] Assignee: California Institute of Technology, Pasadena, Calif.

[22] Filed: Apr. 4, 1974

[21] Appl. No.: 457,849

[52] U.S. Cl. .................. 210/500 M; 260/2.1 E; 260/2.2 R
[51] Int. Cl.$^2$ ............... B01D 31/00; B01D 13/00
[58] Field of Search ............ 210/37, 500 M, 506, 210/508; 195/DIG. 11, 63, 68; 264/4; 260/2.1 E, 2.2 R

[56] References Cited

UNITED STATES PATENTS

| | | | |
|---|---|---|---|
| 3,342,729 | 9/1967 | Strand | 210/500 M X |
| 3,423,491 | 1/1969 | McLain et al. | 210/500 M X |
| 3,425,937 | 2/1974 | Weiss et al. | 210/37 X |
| 3,754,055 | 8/1973 | Rembaum | 260/2.1 R X |
| 3,840,634 | 8/1974 | Chiolle et al. | 210/37 X |

Primary Examiner—Frank A. Spear, Jr.
Attorney, Agent, or Firm—Marvin E. Jacobs

[57] ABSTRACT

The number of quaternary sites and ion-exchange capacity of a polyquaternary, cross-linked, insoluble copolymer of a vinyl pyridine and a dihalo organic compound is increased by about 15–35% by reaction of the polymer with an amine followed by quaternization, if required. The polymer forms spontaneously in the presence of a substrate such as within the pores of a hollow fiber. The improved resin impregnated fiber may be utilized to remove ions from waste or process streams.

10 Claims, No Drawings

INSOLUBLE POLYELECTROLYTE AND ION-EXCHANGE HOLLOW FIBER IMPREGNATED THEREWITH

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention relates to improved insoluble polyelectrolytes and, more particularly, to novel ion-exchange hollow fibers.

2. Description of the Prior Art

Quaternary nitrogen containing materials being cationic in nature find many uses as ion-exchange materials, germicidal agents and as conductive materials. However, many of the polymeric quaternary materials are of low molecular weight and are water soluble. Quaternized, cross-linked, insoluble polymers formed by the spontaneous reaction of unsubstituted vinyl pyridines and a dihalo organic compound are disclosed in copending application Ser. No. 373,616, filed June 26, 1973, and the impregnation of these polymers into and in situ reaction within the pores of hollow fibers are disclosed in copending application Ser. No. 363,130, filed May 23, 1973, now U.S. Pat. No. 3,944,485 issued Mar. 16, 1976. The exchange capacity of these resins, though comparable to those of commercial strong-base, ion-exchange resins, is far below theoretical values.

SUMMARY OF THE INVENTION

It has now been discovered that the ion-exchange capacity of cross-linked, polyquaternary, insoluble, vinyl pyridine-dihalide polymers can be increased a significant amount by a post-polymerization treatment including the step of reacting residual bound halogen with an amine to introduce addition quaternary function into the resin or ion-exchange hollow fiber.

The amine can be a primary, secondary or tertiary amine, preferably the latter to avoid the necessity of a separate quaternization step. The amine can be gaseous or liquid and the reaction can be conducted under ambient conditions or at elevated temperature or pressure.

These and many other objects and attendant advantages of the invention will become readily apparent as the description proceeds.

DESCRIPTION OF THE PREFERRED EMBODIMENTS

The polyquaternary, water-insoluble, cross-linked materials of the invention are prepared by reacting a vinyl pyridine with a dihalo organic compound of the formula:

$$X-R_1-X$$

where X is halo, preferably bromo, chloro or iodo and $R_1$ is divalent organic radical such as alkylene, alkenylene, alkynylene, arylene, alkarylene or aralkylene. $R_1$ may also be alkylthioalkylene or alkyloxyalkylene of the formula $(CH_2)_x(Z)_y(CH_2)_z$, where Z is oxygen or sulfur and x, y and z are integers from 1 to 100. $R_1$ may also be of prepolymer or polymeric length of from 20 to 500 or more carbon atoms such as a bromoterminated polybutadiene, but, preferably has a carbon content of from 1 to 20 carbon atoms to provide an increased charge center density per unit volume and weight of the polymeric product. $R_1$ may be substituted with other groups that do not interfere with the polymerization reaction or properties of the polymer product such as hydroxyl, alkyl, aryl, nitro, cyano or similar groups.

Representative dihalo organic compounds are $\alpha,\omega$-alkylene or alkenylene halides such as dibromo methane, 1,2-dibromoethane, 1,3-dibromopropane, 1,4-dibromobutane, 1,4-dibromo-2-butene, 1,4-dichloro-2-butene, 1,4-dibromo-2,3-dihydroxy butane, 1,5-dibromopentane, 1,6-dibromohexane, 1,8-dibromooctane, 1,10-dibromodecane, and 1,16-dibromohexadecane. The alkenylene compounds such as 1,4-dibromobutene are found to be more reactive than the corresponding saturated compounds. Dihaloaromatics such as o, m and p-dichloro- or o, m and p-dibromoxylene are also suitable. Cross-linked, insoluble products would also be formed from terminally brominated prepolymers such as polyethylenes, polypropylenes, polybutylenes, polybutadienes, polyoxyethylene, etc. containing from about 20 to 500 or more carbon atoms. As the number of carbon atoms in the dihalide increases, elastomeric properties are favored and polyelectrolyte properties decrease.

The butadiene polymers utilized in the process of the invention such as the dibromo polymers discussed above should contain a minimum amount, suitably below 40%, of 1,2-addition units to avoid excessive decrease in elastomeric properties. Such polybutadienes are available as liquid polymers having a molecular weight from 2,000 to 10,000. A suitable material, Polysarrubber (Polysar Limited) is a brominated liquid polybutadiene having a molecular weight of about 5,000 and a functionally very near to two. Another suitable material is HYSTL polybutadiene (HYSTL Development Company, a subsidiary of TRW Inc., and Cores Inc.) or other prepolymers which can be terminated with halogens.

4-vinyl pyridine is the most reactive of the vinyl pyridine isomers. However, 2-methyl-5-vinyl pyridine is available at lower cost and provides products of similar properties. 2-vinyl pyridine has been found to be much less reactive than the other monomers.

The polycationic, cross-linked products are prepared simply by mixing the vinyl pyridine monomer with the dihalide in various proportions and allow the mixture to react until solid materials are formed.

The reaction is believed to proceed through a first stage in which two molecules of vinyl pyridine react with a molecule of a dibromide to form a quaternary intermediate as illustrated below:

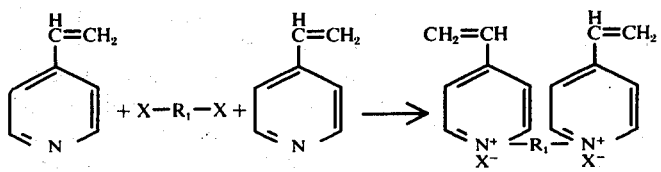

Two molecules of the intermediate dicationic, diunsaturated cross-linking agent then react through the vinyl group to form an intermediate having a structure of the formula:

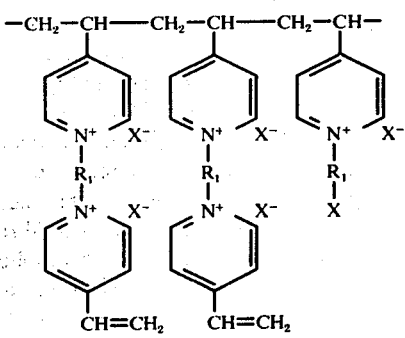

The intermediate reacts further to give a cross-linked network with residual unsaturation and unreacted end halogen groups. Although this mechanism is dominant, other intermediates are also formed. The reaction proceeds spontaneously at room temperature, about 25° C, but may be accelerated by heating the reaction to a higher temperature, usually below 100° C, and suitably from 25°–60° C. The unsaturation on the growing polymer as well as on the finished resin may be utilized in further reaction, e.g., grafting onto substrates by means of Co γ radiation.

Cross-linking of the product is also facilitated by irradiating the mixture with radiation capable of forming reactive species to cross-link the vinyl groups, suitably gamma radiation from a cobalt source. The reaction may be conducted in bulk, in a solvent for the monomer or in water suspension. The reaction proceeds faster in bulk, but, yields are higher in solvents. Higher yields are favored in polar solvents such as dimethylsulfoxide, dimethylformamide, methanol, ethanol, or combinations thereof. Particularly, high yields have been obtained with a 1/1 volume mixture of dimethylformamide and methanol.

The rate of reaction is found to be much higher with bromides, as compared to the corresponding chlorides. The ratio of monomers is controlled such that there is an excess of dibromide in the mixture. A suitable ratio is a stoichiometric ratio of 2 mols of vinyl pyridine to at least 1 mol of the dibromide. It has been found that when the polymerization is conducted with an excess of vinyl pyridine, unchanged vinyl pyridine can be recovered. It has further been found that oxygen and carbon dioxide interfere, inhibit and slow the reaction. Also free radical inhibitors such as hydroquinone do not interfere or slow down the reaction rate. Higher polymerization rates are favored by conducting the reaction in an inert atmosphere such as nitrogen or by conducting the reaction in vacuum. The properties of the polymer products can be varied by using excess of dihalide.

The resulting product in this case contains nonionic halogen capable of further reaction.

The properties of the polymer products can be further varied by conducting the polymerization in the presence of excess monomer and molecular capable of monoquaternization such as an alkyl or alkenyl halide, hydrogen halide, dimethylsulfate, etc. The amounts of the quaternizing species are varied in such a way as to maintain the proportions: 2 moles of vinyl pyridine to 1 mole of dihalide and, 1 of vinyl pyridine to 1 moles of quaternizing species. Thus, for a polymer formed from a mixture containing 1 mole of dihalide and 0.5 mole of quaternizing agent, 2.5 moles of vinyl pyridine are required. By varying these proportions, different amounts of cross-linking are obtained and the resulting resins differ mainly in their swelling properties.

The unreacted halogen end groups are further reacted according to the invention with an amine of the formula:

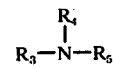

where $R_3$ and $R_4$ are selected from lower alkyl of 1 to 10 carbon atoms, aryl such as phenyl, tolyl, cycloalkyl of 1–10 carbon atoms, lower alkenyl, lower alkoxy or $R_3$ and $R_4$ may be combined into a single divalent group to form a heterocyclic amine and $R_5$ is hydrogen, $R_3$ or —$R_6$— $N(R_3)_2$ where $R_6$ is a divalent aliphatic or aromatic group of 2–10 carbon atoms such as alkylene, phenylene or alkenylene. Representative amines are trimethyl amine (TMA), benzyl dimethyl amine, pyridine, cyclohexyl, dimethyl amine, dimethyl piperidine, tetramethyl diaminopropane, tetramethyl diaminohexane, tetramethyl diaminobutene, tetramethyl phenylene diamine and the like.

In the case of a gaseous amine such as trimethyl amine, the reaction can be conducted at atmospheric or elevated pressure by contacting the cross-linked preformed resin with the gas. The resin may be immersed in solvent such as methanol and the gas bubbled into the solvent. With liquid amines such as pyridine, the reaction can be conducted in bulk by immersing the resin in the amine or in a solution of the amine in solvent. The reaction is stoichiometric and is preferably conducted in the presence of an excess of the amine. The reaction proceeds readily at room temperature of 20° C but proceeds at a faster rate at higher temperatures of from 40° C to 100° C. Specific examples follow:

Freshly distilled 4-vinyl pyridine (4-VP) in a mol.. ratio of 2:1 was mixed with a dihalide of the formula $(Br(CH_2)_xBr$ where $x$ is 2, 3, 4, 6 and 8 in bulk and in solution in 1/1 DMF/methanol solvent. The mixture was left at room temperature for a period of 5 days during which time the color changed from colorless to pink or red. The resin was isolated by addition of acetone followed by washing in acetone. After drying, the resin was isolated in the form of a light yellow powder in yields of 70 to 100% of the theoretical amount.

Ion-exchange capacity was determined by placing approximately 1 gram of resin dried at 100° C overnight and sieved to give a mesh size of 250–500 in a burette, adding 3N NaOH (100 ml) to the column and eluting with distilled water. The elutant was neutralized to pH 6 with N/10 HNO$_3$ and diluted to 250 ml. A 30 ml aliquot was analyzed for Br by the Mohr method. Exchange capacity = meq/g of dry resin. Relative swelling was determined by measuring the increase in wieght after 120 hours of samples of dry resins placed in containers at 100% humidity. The properties are presented in the following table.

Table I

Yields Exchange Capacities and Swelling Properties of 4-VP Resins (Room Temperature)

| Example | Dihalide | Method | Yield W. % | Exchange Capacity meq/g | Relative Swelling % |
|---|---|---|---|---|---|
| 1 | 1,2-Dibromoethane | Solution | 70 | 4.9 | — |
|   |   | Bulk | 51 | — | — |
| 2 | 1,3-Dibromopropane | Solution | 97 | — | — |
|   |   | Bulk | 70 | 4.52 | 67.1 |
| 3 | 1,4-Dibromobutane | Solution | 94 | — | — |
|   |   | Bulk | 80 | 4.59 | 58.0 |
| 4 | 1,6-Dibromohexane | Solution | 100 | — | — |
|   |   | Bulk | 79 | 3.11 |   |
| 5 | 1,8-Dibromooctane | Solution | 100 | — | — |
|   |   | Bulk | 90 | 2.37 | 47.8 |

EXAMPLE 6

The resins of Examples 1, 2, 3 and 5 were further reacted with trimethyl amine by immersing the resin in methanol, stirring the resin suspension and bubbling TMA into the vessel for about 12 hours. The results follow.

Table II

| Theoretical and Observed Ionic Bromide Content of 4-VP Resins |   |   |   |
|---|---|---|---|
| dihalide | % Br$^-$ Theoretical | % Br$^-$ Found | % Br$^-$ After Further Reaction |
| 1,2-Dibromoethane | 40.2 | 35.3 | — |
| 1,3-Dibromopropane | 38.44 | 31.1 | 36.5 |
| 1,4-Dibromobutane | 36.85 | 28.4 | — |
| 1,8-Diromooctane | 31.58 | 19.4 | 26.5 |

As can be seen, the amount of ionic bromine and ion-exchange capacity increased from 17 to 39% by means of the treatment according to the invention.

EXAMPLE 7

The polymers of Example 5 (4-VP + dibromohexane) was immersed in pyridine and the mixture heated to 50° C for about 12 hours. The resin was washed with methanol and acetone. Ionic bromine content increased about 20%.

EXAMPLE 8

The procedure of Example 7 was repeated substituting dimethyl piperidine for pyridine. Ionic bromine again was found to be increased by about 20%.

The polymerization may be conducted in situ or on the surfaces of polymeric films, filaments or fibrous materials, such as cloth or paper on the surfaces of within the pores of particles such as glass, clay, hollow fibers, cement, sand, carbon black, alumina, silica gel, and the like which act as supports to form a material having a polyelectrolytic ion-exchange surface. In particular, when paper is impregnated with the monomers of the invention, an ion-exchange paper is produced. The ion-exchange paper is usable as an indicator paper, since it undergoes a reversible color change from dark brown in presence of base to yellow in the presence of acid. The ion-exchange paper may also be used for detection of ions such as phosphate, by a procedure to be described and may be used in electrophoretic separations in chromotography for analysis, detection and separation of ions or in the purification of process or water streams.

The invention is particularly adapted to the manufacture of ion-exchange hollow fibers.

The hollow fiber configuration of a membrane offers the opportunity to prepare thin-walled devices with very large surface areas. Such a device would also provide the flexibility of high transport rates per unit volume and the possibility of continuous operation without the need for regeneration cycles. Further advantage over other configurations is that supports are not required for the hollow fibers.

Ion-exchange hollow fibers are prepared according to the invention by introducing into the wall of the preformed fiber polymerizable liquid monomers and polymerizing the monomers therein to form solid, insoluble, ion-exchange resin particles embedded within the wall of the fiber which are then reacted with amines.

In a preferred embodiment of the invention, the mixture of polymerizable monomers is fed into one end of the fiber and pumped through the other end. In a permeable fiber, the mixture will also exude through the pores in the walls. After the particles of polymer have been formed, the excess particles blocking the central passage are removed by forcing liquid through the bore of the fiber.

The ion-exchange fibers of the invention have several further advantages as compared to resin beads or flat membranes. There is reduced pressure drop available through the controlled dimensions of the fluid passages. In addition, the wall thickness which holds the ion-exchange sites can be reduced to 30–40 microns without prejudicing the integrity of the structure, such as is experienced with reticulated beads. Finally, the difficulties experienced by the swelling and deswelling of spheres is reduced in the cylindrical configuration of the fiber. This, in turn, allows more rapid unloading of the active sites during the regeneration cycle.

The dimensions of the fibers are selected depending on the use and capacity of the end device. Length of the fibers is the least important dimension and is dependent on the amount of ion to be removed, the flux rate through the wall, the flow rate of solution, the number of fibers in a bundle, and the practical length of the unit. The wall thickness, permeability and ion-exchange capacity are the most influential factors in the performance and effectiveness of ion-exchange hollow fibers.

The wall thickness is preferably as thin as practical under the circumstances and is preferably as low as 10 microns, typically from 20 to 300 microns, preferably 30–100 microns. The inside diameter is always maintained as low as possible to maximize available surface area. The inside diameter typically ranges from 50 to 1000 microns.

The morphology of the fiber used for resin deposition will determine the pore density and average pore size of the resulting ion-exchange fibers. Characterization of membrane morphology is in itself a difficult study, so that phenomonological parameters have been used by many investigators to described membrane properties.

The descriptors found most useful are the water content of the membrane, the hydraulic resistance of the membrane, and the permeability rates of several solutes through the membrane walls. These values can somtimes be reconciled with a pore model of transport, when an independent measurement of either pore area or pore diameter can be achieved.

Pore diameters (d) of the largest pores present can be measured by the pressure of air required to displace a fluid of known surface tension from the walls of the pores if the fluid wets the pore wall. For isotropic structures, the relationship between air pressure P (in psi) and surface tension $\gamma$ (in dynes/cm) is given by:

$$p = 0.415 \, \gamma/d$$

Attempts to measure displacement pressure, up to the pressure level that the fibers can contain, were unsuccessful. This indicates that the average pore size is smaller than 1000 angstroms.

The hydraulic permeability of the fiber bundles can be measured by determining the rate of water permeated per unit area (A) under a specified driving force. The relationship $$J_r = L_p A \Delta \qquad (1)$$

has been found linear over a range of pressures. $J_r$ is measured in cc/sec, and $\Delta P$ is expressed in atmospheres. The dimensions of $L_P$ are then $cm^3 \, cm^{-2} \, sec^{-1} atm^{-1}$. Another useful expression of this relationship is in terms of the inverse of the permeability coefficient, i.e., $1/L_P$. The inverse can be considered a resistance coefficient $R_{H\ 0}$; when membranes are used in series, the total resistance is an additive function of the individual resistances.

A third sensitive descriptor of membrane structure is the permeability coefficient of specific solutes. The arrangement for measuring the permeability coefficient utilizes a fiber bundle through which the solution is pumped at a constant and controlled rate. The fibers are bathed in a large excess of solution in which the concentration of the solute being tested is maintained close to zero. The solute, therefore, diffuses out of the fiber bores as a result of the concentration gradient across the fiber wall. Since the gradient is changing along the axis of the fiber, provision must be made for estimating the form of the gradient.

The material balance of the solute concentration can be written by:

$$-M = Q_v (C l_o - C_i) \qquad (2)$$

where $M$ is the rate of solute loss through the walls, $Q_v$ is the axial flow of solution, $C_i$ and $C_o$ are the inlet and outlet concentrations respectively. Similarly, if the process is diffusion controlled, one can project that the rate of solute transport is directly proportional to the area available for permeation, and the average concentration gradient:

$$-M = P A (\Delta c) \qquad (3)$$

where $(\Delta c)$ is an average concentration gradient.

Using a log average depletion of solute, we get:

$$(\Delta c) = (C_o - C_i)/\ln C_i/C_o \qquad (4)$$

Equating equations (2) and (3) leads to:

$$P = Q/A \ln C_i/C_o \qquad (5)$$

With equation (5) it is relatively simple to estimate the permeability coefficient using steady state analyses. As in the case of the hydraulic permeability, the solute permeability can be conveniently expressed as a resistance, i.e. $1/p$.

Typical initial hydraulic permeabilities of the fiber wall are from 1 to 100 × $10^{-5}$ ml/cm$^2$ sec atm. The corresponding solute diffusive permeabilities (cm/sec) for a 110 molecular weight molecule is 5.6 to 55.6 × $10^{-5}$ and for a 1200 molecular weight molecule is 1.2 to 6.7 × $10^{-5}$. These fibers will not allow a 60,000 MW protein (albumin) to permeate, so there is a maximum in the pore size that is smaller than the means diameter of this protein. There are at present no clear-cut techniques by which the pore size and pore frequency can be measured without irreversible alterations of the structure during the measurement. Therefore, the solute porfile of permeabilities is a definite parameter defining the microporosity of the fibers. The initial permeability is modified during treatment due to embedment of ion-exchange particles within the pores, swelling and collapse of walls of some pores or microvoids. The porosity of the final polymer is preferably chosen such that there is no leakage of ions other than the separated ion through the wall.

Hollow fibers are an outgrowth of textile spinning of synthetic organic polymers in order to produce high-bulk, low density fabrics. Hollow fibers are manufactured from textile grade resins and may be spun by wet spinning (spinning from a polymer solution into a liquid coagulant); dry spinning (spinning from a solution of a polymer in a volatile solvent into an evaporative column); or by melt spinning. The tubular cross-section is formed by extruding the molten polymer or polymer solution through an annular dye or spinneret.

The fibers should preferably be formed from high-strength, high-modulus fibers since these can be formed with thin walls, yet allow higher operating pressure drops and permit negation of osmotic flows accompanying the ion-exchange phenomenon. The fibers should also exhibit chemical compatibility with and stability to the ion-exchange polymerization system. The polymerization system should not dissolve or permanently alter the fiber morphology during formation and embedment of the ion-exchange particles.

Textile grade acrylic fibers, suitably polymers of acrylonitrile, have been found to be compatible with the polyquaternary polymer reactants of this invention. The polyacrylonitrile may be homopolymers or copolymers containing up to 20% by weight of comonomers such as ethyl acrylate or vinyl acetate.

The acrylonitrile polymers are wet spun from a 15–25% solids solution in a highly polar solvent such as methyl acetamide, dimethyl formamide or 40% CaSCN through an annular spinneret into a liquid coagulant such as water. The pore size and distribution can be controlled by selection of a solvent. A specific example follows.

EXAMPLE 9

Polyacrylonitrile hollow fibers were used. Their hydraulic permeability was $9 \times 10^{-5}$ cm/sec atm., the wall thickness 50 $\mu$, the inside diameter 200 microns and the wall micropore diameter about 100 A. Hollow fibers (150) assembled in bundles with a total surface area of 140 cm$^2$ were washed first with water, then with methanol and dried by passing nitrogen gas through them for one hour. They were immersed in a mixture of 4-VP and $\alpha,\omega$-dihaloalkane (2:1 molar). The reaction was permitted to proceed for 10 days in the case of dibromo ethane and 2 days in the case of dibromohexane.

EXAMPLE 10

The ion-exchange fiber bundles of Example 9 were further reacted with amine by rinsing the fiber bundle in methanol, placing the bundle in a vessel and passing TMA through the vessel for ½ hour. The vessel was then filled with methanol and TMA bubbled through for ½ hour. The methanol was removed and TMA passed through the vessel for an additional ¾ hours before closing the vessel and allowing the reaction to proceed overnight.

The ion-exchange hollow fibers of the invention have a high ion-exchange capacity, good mechanical strength and uniform ion-exchange capacity throughout. The treated fibers will find use as membranes in water treatment, dialysis and generally to separate ionic solutions. In the case of constraining cationic resins such as polyquaternary particles within the pores of the walls, the fibers can be utilized to separate chromate, phosphate, uranate, uranium sulfate complexes, cyanide or carbonate from solutions in industrial applications such as waste water treatment, process streams, plating baths or mine wastes.

A very attractive, continuous ion removal process is provided with the fibers of the invention utilizing the Donnan principle. It has been shown that when a dilute polyvalent ion is separated by an ion selective membrane from a concentrated solution of a lower valency, the mobile ions will distribute between the two solutions in such a way that the multivalent ion will concentrate in the more concentrated solution.

One very important application of such a process is in chromate removal. Chromates are used as corrosion inhibitors in various industrial water streams such as in boilers and cooling water service. In time, these streams build up in calcium and other cations which precipitate with carbonate. Periodically, a purge is required. This chromate contaminated blowdown is a toxicity hazard and cannot be disposed of indiscriminately. The disadvantages of packed ion-exchange resin beads have been discussed. An alternative does exist in the precipitation of a reduced chromate. This is effective for processing various liquors but is not economically attractive and not easily manageable for streams having low chromate concentration levels.

In accordance with the invention, the Donnan pumping principle is extremely effective using strong Cl$^-$ concentrations to pump dilute chromate against its concentration gradient.

EXAMPLE 11

Removal of dichromate from aqueous solution is achieved by using the Donnan pumping principle, e.g., dichromate ions are pumped against their concentration gradient through the ion-exchange hollow fibers by a second ion (of the same change sign) present at a much higher concentration on the other side of the hollow fiber wall. In this manner polluting ions can be concentrated in the pumping ion solution and the cleaned up water can be reused or discharged.

Ion-exchange experiments were run in the crossflow mode using 1100 ml of 1 N NaCl solution to clean up 765 ml wastewater which was initially either 10$^{-3}$ or 10$^{-4}$ M Cr$_2$O$_7^=$ solution. The fibers of Examples 9 and 10 were bathed in the stirred wastewater while the sodium chloride solution was circulated continuously through the fibers. For wastewater containing 10$^{-4}$ M Cr$_2$O$_7^=$, the initial dichromate content of the pumping ion solution (NaCl) was varied from 0 to 10$^{-2}$ M Cr$_2$O$_7^=$. The Cl$^{116}$ leak rate was 0.0006 moles per hour per fiber bundle.

The data indicates that while the fiber bundle of Example 9 impregnated with resin can reduce the dichromate concentration from 10$^{-4}$ to $2.5 \times 10^{-6}$ M Cr$_2$O$_7^=$ (10 ppm to 0.2 – 0.5 ppm of chromium) that the amine treated fiber bundle of Example 10 provides a further reduction in chromium content by a factor of at least about 2. Present federal standards for effluents are less than 0.05 ppm of chromium.

The hollow fibers of this invention permit a packing density i.e. area available per bulk volume of exchanger, much higher than in other configurations. The treated fibers have a high-ion-exchange capacity, a practical wall permeability and good mechanical strength. Bundles of these fibers will find use in continuous removal of ions from solution without the need for regeneration. The treated fibers will also find use in fuel cells, chemical batteries and in liquid chromatography. The fiber may be cut in sections after chromatographic separation to provide samples for quantitative or qualitative analysis.

The resins of the invention are well suited for use as ion exchange capacity measurements indicate that the three dimensional cross-linked materials. Swelling and ion exchange capacity measurments indicate that the materials will expand sufficiently to expose the quaternary sites and to allow the solution being treated to penetrate into the material. The ion exchange capacity compares favorably to available materials and the material can be regenerated by conventional base treatment to elute the bound anions and return the paper or column to basic form.

The ion exchange paper will also find use in paper chromatographic separation of a wide variety of materials. Both quantitative and qualitative information is obtainable from the spot size, spot location and length of elution. The resin of the invention may be utilized as an acid-base indicator particularly, when supported on a porous substrate such as paper. The indicator paper would be suitable as a disposable body fluid analysis paper or may be rinsed and repeatedly utilized for analysis since the color change is reversible. A supported film is also useful for imaging by selective application of a pattern of acid or base to the material to develop a contrastingly colored pattern with respect to the background. The pattern can be erased by application of acid or base as is required.

The ion exchange material of the invention may also be utilized for detection of ions. For example, when ion exchange paper is dipped in a dilute aqueous solution of sodium phosphate (8 ppm), washed with water and treated with ammonium molybdate followed by stannous chloride, a blue color is developed which indicates the presence of small amounts of phosphate in water. Beads or particles of the ion-exchange material efficiently remove phosphate ions from aqueous solution.

A wide variety of resins of controllably differing properties is produced by appropriate selection of dihalide. The spacing between positive nitrogen atoms may readily be varied in order to render the resin selective for specific anions. The resins are useful in chromatography, in analysis, detection and separation of ions, as ion exchange particles or membranes, as acid-base indicators or in acid-base imaging.

It is to be realized that only preferred embodiments of the invention have been described and that numerous substitutions, alterations and modifications are all permissible without departing from the spirit and scope of the invention as defined in the following claims.

What is claimed is:

1. An ion-exchange medium comprising a hollow, annular, thin-walled microporous fiber having particles of polymer embedded and constrained within said pores, said particles being smaller than the diameter of said pores and said polymer comprising polyquaternary, water-insoluble, cross-linked polyer of vinyl pyridine and a dihalo organic compound of the formula:

X—R—X where X is halo selected from the group consisting of bromo, chloro and iodo and $R_1$ is a divalent organic group; said polymer containing a structure of the formula:

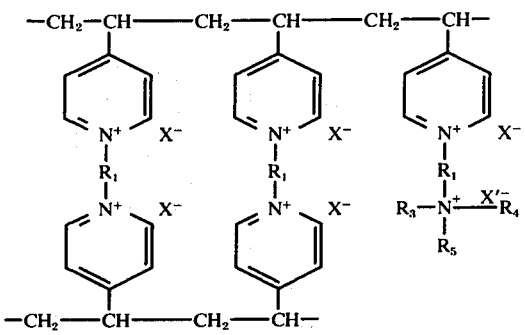

where $R_3$ and $R_4$ are selected from lower alkyl of 1 to 10 carbon atoms, aryl, cycloalkyl of 1 to 10 carbon atoms, lower alkenyl, lower alkoxy or $R_3$ and $R_4$ are combined in a single aliphatic divalent group; $R_5$ is selected from hydrogen, $R_3$ or $-R_6-N(R_3)_2$ where $R_6$ is a divalent aliphatic or aromatic group of 2–10 carbon atoms and $X^-$ and $X'^-$ are selected from chloro, bromo or iodo said $X^-$ and $X'^-$ being ionized halo derived from $X-R_1-X$ with $X^-$ groups ionized by quaternization with vinyl pyridine and $X'^-$ groups ionized by post polymerization quaternization of said polymer with

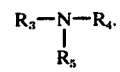

2. A medium according to claim 1 in which $R_1$ contains 1–20 carbon atoms and is selected from alkylene, alkenylene, alkynylene, arylene, alkarylene and aralkylene.

3. A medium according to claim 1 in which $R_1$ is selected from ethylene an hexylene.

4. A medium according to claim 3 in which $R_3$, $R_4$ and $R_5$ are methyl.

5. An ion-exchange medium according to claim 1 in which the wall thickness is from 10 to 300 microns.

6. A medium according to claim 5 in which the internal diameter is from 50 to 1,000 microns.

7. A medium according to claim 5 in which the pores are evenly distributed throughout the wall of the fiber and have an average diameter less than 1,000 angstroms.

8. A medium according to claim 1 in which said fiber resin is a fiber grade polyacrylonitrile resin.

9. A medium according to claim 1 in which the resin particles embedded in said pores do not block said pores to passage of selected ions through the wall to a solution of ions of higher concentration and like charge of the selected ions.

10. A medium according to claim 1 in which $X'^-$ is 17 to 39% by wieght of the sum of the weights of $X^-$ and $X'^-$.

* * * * *

UNITED STATES PATENT AND TRADEMARK OFFICE
CERTIFICATE OF CORRECTION

PATENT NO. : 4,014,798
DATED : March 29, 1977
INVENTOR(S) : Alan Rembaum

It is certified that error appears in the above-identified patent and that said Letters Patent are hereby corrected as shown below:

Column 2, line 49, change "functionally" to -- functionality --
Column 2, line 62, change "allow" to -- allowing --

Column 4, line 14, change "molecular" to -- a molecule --
Column 4, line 19, after "1" first occurence, insert -- mole --.
Column 4, line 19, change "moles" to -- mole --

Column 7, after line 45, correct formula to read -- $J_v = L_p A \Delta P$ --
Column 7, line 56, correct -- $R_{H_2O}$ --

Column 8, after line 4, correct formula to read -- $-\dot{M} = Q_v(C_o - C_i) -$
Column 8, line 43, correct -- profile --

Column 10, line 31, change "$Cl^{116}$" to -- $Cl^-$ --
Column 10, line 54, delete "capacity measurements indicate that the" and insert -- materials since they are water insoluble, --

Column 11, Claim 1, line 49, correct -- polymer --
Column 11, Claim 1, after line 50, in the formula change "R" to -- $R_1$ --

UNITED STATES PATENT OFFICE
CERTIFICATE OF CORRECTION

Patent No. 4,014,798     Dated March 29, 1977

Inventor(s) Alan Rembaum     Page 2 of 2

It is certified that error appears in the above-identified patent and that said Letters Patent are hereby corrected as shown below:

Column 12, Claim 3, line 37, change "an" to -- and --
Column 12, Claim 10, line 56, correct -- weight --

Signed and Sealed this

Twenty-fourth Day of May 1977

[SEAL]

Attest:

RUTH C. MASON
*Attesting Officer*

C. MARSHALL DANN
*Commissioner of Patents and Trademarks*